United States Patent
Dolla

(10) Patent No.: US 11,305,044 B2
(45) Date of Patent: Apr. 19, 2022

(54) HEAT EXCHANGER TUBE FOR A HEAT EXCHANGER OF AN OXYGENATOR

(71) Applicant: RAUMEDIC AG, Münchberg (DE)

(72) Inventor: Andreas Dolla, Hof (DE)

(73) Assignee: RAUMEDIC AG, Münchberg (DE)

(*) Notice: Subject to any disclaimer, the term of this patent is extended or adjusted under 35 U.S.C. 154(b) by 55 days.

(21) Appl. No.: 16/062,655

(22) PCT Filed: Dec. 14, 2016

(86) PCT No.: PCT/EP2016/080886
§ 371 (c)(1),
(2) Date: Jun. 15, 2018

(87) PCT Pub. No.: WO2017/102785
PCT Pub. Date: Jun. 22, 2017

(65) Prior Publication Data
US 2018/0369472 A1   Dec. 27, 2018

(30) Foreign Application Priority Data

Dec. 17, 2015   (DE) .................. 10 2015 225 555.7

(51) Int. Cl.
*A61M 1/16* (2006.01)
*B29C 48/09* (2019.01)
(Continued)

(52) U.S. Cl.
CPC ......... *A61M 1/1698* (2013.01); *B29C 48/022* (2019.02); *B29C 48/09* (2019.02);
(Continued)

(58) Field of Classification Search
CPC ............ A61M 1/1698; A61M 2207/00; A61M 2205/366; B29C 48/90; B29C 48/92;
(Continued)

(56) References Cited

U.S. PATENT DOCUMENTS 4,520,672 A    6/1985  Saint-Amour
5,270,004 A *  12/1993 Cosentino ........... A61M 1/1698
                                                128/DIG. 3
(Continued)

FOREIGN PATENT DOCUMENTS

DE         68925291      5/1996
DE      602004006097     6/2007
(Continued)

OTHER PUBLICATIONS

BASF Polyurethane GmbH, Thermoplastic Polyurethane Elastomers (TPU) Elastollan®—Processing Recommendations, Revision Jan. 2017.
(Continued)

*Primary Examiner* — James C Yager
(74) *Attorney, Agent, or Firm* — Smartpat PLC

(57) ABSTRACT

The invention relates to a heat exchanger tube (1) which is a component of a heat exchanger of an oxygenator. The heat exchanger tube (1) comprises a tube body (2) consisting of thermoplastic polyurethane (PTU). The tube body (2) has a Shore hardness of greater than 60 D. This results in a heat exchanger tube optimised for use in a heat exchanger of an oxygenator.

6 Claims, 1 Drawing Sheet

(51) Int. Cl.
*B29C 48/00* (2019.01)
*B29C 48/88* (2019.01)
*F28F 21/06* (2006.01)
*B29C 48/92* (2019.01)
*B29C 48/90* (2019.01)
*F28D 21/00* (2006.01)
*B29K 75/00* (2006.01)
*B29L 23/00* (2006.01)

(52) U.S. Cl.
CPC .......... *B29C 48/90* (2019.02); *B29C 48/9115* (2019.02); *B29C 48/92* (2019.02); *F28F 21/062* (2013.01); *A61M 2205/366* (2013.01); *A61M 2207/00* (2013.01); *B29C 48/919* (2019.02); *B29C 2948/92647* (2019.02); *B29K 2075/00* (2013.01); *B29K 2995/0006* (2013.01); *B29K 2995/007* (2013.01); *B29K 2995/0097* (2013.01); *B29L 2023/007* (2013.01); *F28D 2021/005* (2013.01); *F28F 2255/16* (2013.01); *Y10T 428/139* (2015.01); *Y10T 428/1352* (2015.01)

(58) Field of Classification Search
CPC ... B29C 48/9115; B29C 48/022; B29C 48/09; B29C 48/919; B29C 2948/92647; F28F 21/062; F28F 2255/16; B29L 2023/007; B29K 2995/0097; B29K 2995/007; B29K 2995/006; B29K 2075/00; Y10T 428/1352; Y10T 428/139
See application file for complete search history.

(56) References Cited

U.S. PATENT DOCUMENTS

| | | |
|---|---|---|
| 5,498,377 A | 3/1996 | Ozaki et al. |
| 5,545,151 A | 8/1996 | O'Connor et al. |
| 5,578,267 A | 11/1996 | Cosentino et al. |
| 5,630,982 A | 5/1997 | Boring |
| 5,706,889 A | 1/1998 | Bach et al. |
| 5,876,667 A | 3/1999 | Gremel et al. |
| 2005/0080507 A1 | 4/2005 | Silberg et al. |
| 2006/0255497 A1 | 11/2006 | Prevotat |
| 2010/0119642 A1 | 5/2010 | Ohmi |
| 2012/0055576 A1 | 3/2012 | Prusty et al. |
| 2013/0327428 A1 | 12/2013 | Siddhamalli et al. |
| 2015/0041107 A1 | 2/2015 | Stöcker et al. |
| 2019/0258084 A1* | 8/2019 | Stevens .................. G02C 7/085 |

FOREIGN PATENT DOCUMENTS

| | | |
|---|---|---|
| DE | 102012204705 A1 | 9/2013 |
| GB | 1185430 A | 3/1970 |
| WO | 0132398 A1 | 5/2001 |
| WO | 2011086010 A1 | 7/2011 |

OTHER PUBLICATIONS

BASF Polyurethanes GmbH, Thermoplastic Polyurethane Elastomers, Ellastollan—Material Properties, Retrieved from http://www.polyurethanes.basf.de/pu/solutions/elastollan/en/function/conversions:/publish/content/group/Arbeitsgebiete_und_Produkte/Thermoplastische_Spezialelastomere/Infomaterial/elastollan_material_d.pdf on Oct. 25, 2018.

Lubrizol, Produktdatenblatt Estane® 58091 TPU, Stand 2014.

Product Data Sheet of Elasthane TPU, Authors: Dsm.

Stefan Wöstmann: "Filter unter Druck", Plastverarbeiter, Feb. 2006, retrieved from: www.plastverarbeiter.de/wp-content/uploads/migrated/docs/1477_30248.pdf.

Technical Data Sheet of Estane 58091 TPU, Authors: Lubrizol.

Thermoplastic Polyurethane Elastomers, Publication data: Handbook of Elastomers, Second edition, Revised and Expanded,,Jan. 1, 2000,Marcel Dekker, Inc, Source info: pp. 2pp, 387-415.

Rosate, Dominick V., "Tolerance, chapter 6 Plastic Performance", Plastics engineered product design, 2003, Elsevier, Oxford, ISBN: 1856174166, pp. 414-421.

* cited by examiner

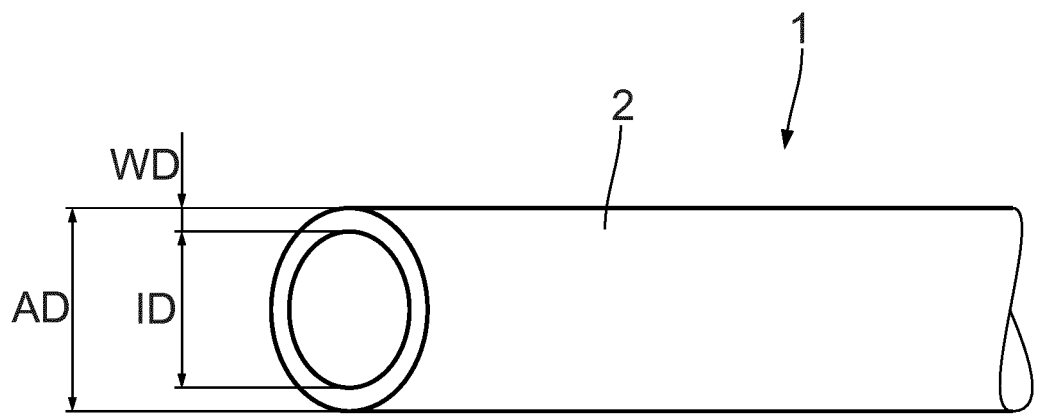

HEAT EXCHANGER TUBE FOR A HEAT EXCHANGER OF AN OXYGENATOR

CROSS REFERENCE TO RELATED APPLICATION

This application is a National Phase Entry of PCT/EP2016/080886, filed 14-Dec-2016, which claims priority to German patent application DE 10 2015 225 555.7, filed 17-Dec-2015, both of which are incorporated herein by reference.

TECHNICAL FIELD

The invention relates to a heat exchanger tube for a heat exchanger of an oxygenator, a method for producing a tube body for such a heat exchanger tube, a heat exchanger body for a heat exchanger of an oxygenator having a plurality of tube sections from such a heat exchanger tube, and a heat exchanger for an oxygenator with such a heat exchanger body.

BACKGROUND

An oxygenator is a medical product that enriches blood with oxygen and removes carbon dioxide from the blood. The oxygenator is used in cardiac surgery as a component of a heart-lung machine and, for example, replaces the function of a lung during open-heart surgery. At the oxygenator, a heat exchanger for the exchange of heat between blood and a heat exchange medium, in particular water, is also provided.

Such an oxygenator with a plurality of sections of a heat exchanger tube is known from WO 2011/086 010 A1. Additional oxygenators are known from U.S. Pat. No. 5,876,667 and DE 689 25 291 T2.

DE 689 25 291 T2 discloses a cylindrical blood warmer and a blood oxygenator. U.S. Pat. No. 6,706,889 discloses a heat exchanger oxygenator. DE 10 2012 204 705 A1 discloses a heat exchanger for an oxygenator.

It is the object of this invention to optimize a heat exchanger tube for use in a heat exchanger of an oxygenator.

SUMMARY

According to the invention, this object is accomplished by a heat exchanger tube as claimed.

According to the invention, it was first recognized that a tube body made of a thermoplastic polyurethane has advantages over other polymer materials proposed in the prior art for use in heat exchangers of an oxygenator. TPU has good thermal conductivity properties, in particular a high heat transfer coefficient. TPU is hydrophilic, such that an electrostatic charge of the heat exchanger does not arise. The heat exchanger tube has a high degree of dielectric strength. The heat exchanger tube made of TPU has good compatibility with blood. Such advantages apply in particular to the TPU tube body with a Shore hardness>60 D. It also has low stickiness, which leads to easy handling in the processing of the heat exchanger tube. The heat exchanger tube is stiff and has good pressure and deformation stability. The TPU of the tube body may be a polyether-based TPU material. The TPU material of the tube body may be aromatic TPU. The result is a hydrolysis-stable tube body, which offers particular advantages in connection with a water/blood contact of the tube body. The small wall thickness deviation of the heat exchanger tube leads to the possibility of realizing a highly homogeneous heat exchanger in terms of its heat transfer properties. The deviation of the wall thickness from the nominal wall thickness may amount to at most 0.015 mm or at most 0.010 mm. The specified maximum wall thickness deviations may also occur over much greater tube lengths, in the range of more than 1 m, in the range of more than 10 m, in the range of more than 100 m, in the range of more than 1,000 m or even in the range of more than 10,000 m, such that, even over such greater tube lengths, there is no deviation of the wall thickness from a nominal wall thickness greater than the maximum deviations specified above.

Shore hardnesses greater than 60 D, preferably greater than 80 D, lead to a particularly advantageous heat exchanger tube. An example of a tube body material having a Shore hardness in the range of 73 D is Elastollan® 1174 D. An example of a tube body material having a Shore hardness in the range of 75 D is Tecothane™ 1075 D. An example of a tube body material having a Shore hardness in the range of 76 D is Pellethane® 2363 75 D. Examples of tube body materials having a Shore hardness in the range of 80 D are Tecoplast® TP-470, with a Shore hardness of 82 D, and Isoplast® 300ETPU, with a Shore hardness of 83 D. An example of a tube body material with a Rockwell hardness in the range of 121 R is Isoplast® 2530.

A wall thickness of less than 0.07 mm results in a heat exchanger tube with very high thermal conductivity, and thus an effective heat transfer between the lumen of a tube and the surrounding area of the tube. In addition, a small wall thickness leads to a reduction of the risk of embedding larger material inclusions, in particular those of gel particles, and the risk of the presence of inhomogeneities in the tube wall. As a whole, this results in more homogeneous properties of the heat exchanger tube. The wall thickness may amount to, for example, 0.06 mm or 0.05 mm.

A dielectric strength of at least 10 kV leads to a high degree of operational reliability of a heat exchanger equipped with the heat exchanger tube. The dielectric strength is determined from a measurement in accordance with DIN EN 60243-1. When measuring dielectric strength, a tube body with a wall thickness is used; this amounts to at most 0.1 mm, and is in particular in the range between 0.06 mm and 0.085 mm, for example in the range between 0.065 and 0.080 mm, in the range between 0.060 and 0.075 mm, in the range between 0.077 and 0.082 mm or in the range between 0.075 and 0.085 mm.

A tube body for a heat exchanger tube may be produced from a plastic melt. Production may include a step of filtering out get particles contained in the plastic melt. The filtration step leads to the filtering out of impurities, such that inhomogeneities in the tube material are avoided. Cross-linked and partially cross-linked polyurethane components are designated as gel particles. The filtering out of gel particles contained in the melt leads to a purge of the polymer present in the melt of intrinsic polymer components, which arise as part of the production of polymers. Such filtered-out components can lead to inhomogeneities in the extruded tube material, thus to undesired vulnerabilities in terms of electrical and/or physical properties. Gel particles can act as nuclei in undesirably forming crystalline structures. Gel particles with a density that differs from that of the other polyurethane material of the tube body lead to the undesirable formation of flow zones in the polymer. Such flow inhomogeneities also lead to an undesirable reduction in dielectric strength. Due to the filtering out of the gel particles, the proportion of amorphous material in the plastic melt increases. This leads to an increase in the electrical dielectric strength.

In the production process, the cooling step can take place so rapidly that amorphous material regions are produced in the tube material. This leads to an advantageous increase in the electrical dielectric strength. A cooling rate in the cooling step may be greater than 5 K/min, may be greater than 10 K/min, may be greater than 15 K/min, may be greater than 20 K/min, may be greater than 25 K/min, may be greater than 30 K/min, may be greater than 35 K/min, may be greater than 40 K/min, may be greater than 45 K/min, and may be greater than 50 K/min.

The advantages of a heat exchanger body which includes the disclosed heat exchanger tube and a heat exchanger having such a heat exchanger body correspond to those advantages already mentioned above with reference to the heat exchanger tube according to the invention.

One embodiment of the invention will be explained in more detail below with reference to the drawing.

BRIEF DESCRIPTION OF THE DRAWING

The single figure shows a perspective view of a broken section of a heat exchanger tube for a heat exchanger of an oxygenator.

DETAILED DESCRIPTION

A heat exchanger tube 1 is a component of a heat exchanger body (which is otherwise not shown) of a heat exchanger of an oxygenator. The heat exchanger tube 1 can be a component of an oxygenator, as it is otherwise described in WO 2011/086 010 A1, the contents of which are fully incorporated herein in connection with the description of the other oxygenator. The oxygenator has a tubular base body, in which the heat exchanger body is arranged.

The heat exchanger tube has a tube body 2 made of thermoplastic polyurethane (TPU). The tube body 2 has a Shore hardness greater than 60 D. Examples of such a material are Isoplast® 300ETPU with a Shore hardness of 83 D and Tecoplast® TP-470 with a Shore hardness of 82 D.

The thermoplastic polyurethane of the tube body is a polyether-based TPU. The material of the tube body 2 is an aromatic TPU.

The tube body 2 has an inner diameter ID in the range between 0.40 mm and 0.80 mm and a larger outer diameter AD in the range between 0.50 mm and 1.0 mm. With the tube body 2, a wall thickness WD is less than 0.07 mm. Examples of dimensions of the tube body 2 are the following: ID=0.67 mm, AD=0.79 mm, resulting in a wall thickness WD of 0.06 mm, or ID=0.50 mm, AD=0.6 mm, resulting a wall thickness WD of 0.05 mm.

Over a tube length of, for example, 200 mm, the wall thickness WD deviates by less than 0.02 mm from a nominal wall thickness. In fact, the production can be made so precise that the wall thickness WD deviates from a nominal wall thickness by less than 0.02 mm, even over a tube length of more than 1 m, more than 10 m, more than 100 m, more than 1,000 m and also more than 10,000 m.

The heat exchanger tube 1 has an electrical dielectric strength that amounts to at least 10 kV and that is, for example, in the range of 10 kV, 11 kV, 12 kV or 14 kV. To measure the electrical dielectric strength, a wire electrode is introduced into the lumen of the tube body 2, and an outer electrode, in the form of a foil, is brought in contact with an outer wall of the tube body 2. An electrical voltage is then applied to the two electrodes and continuously increased until a breakdown occurs. This measurement of dielectric strength is carried out in accordance with DIN EN 60243-1. A value of 14 kV for the dielectric strength can be achieved with a larger wall thickness WD, for example, 0.06 mm. A value of 10 kV for the dielectric strength can be achieved with a smaller value of the wall thickness WD, for example, 0.05 mm. With a wall thickness WD in the range of 0.065 mm, a dielectric strength of 12 kV was measured in a series of measurements. With a wall thickness WD of 0.06 mm, a dielectric strength of 10 kV was measured in the series of measurements. With higher wall thicknesses WD, for example 0.077 mm, a dielectric strength of 11 kV was measured in the series of measurements. For an additional composition of the tube body 2, with a wall thickness WD in the range of 0.075 to 0.085 mm, a dielectric strength of up to 14 kV was measured in the series of measurements.

The tube body 2 is transparent to visible light. The tube body 2 is essentially free of inclusions.

In the production of the tube body 2, a TPU plastic melt is first produced.

This plastic melt is then filtered. The filtration is used in particular for filtering out gel particles contained in the melt.

The filtered melt is then extruded into a tube. The extruded tube is cooled. This takes place by running the extruded tube through a tempering chamber containing a heat transfer medium, for example, by passing the extruded tube through a water basin, wherein the water is maintained at a temperature in the range between 5° and 15°, for example at a temperature of 10°.

Such cooling of the material produces amorphous material regions in the tube body 2.

After cooling, the tube thus produced is assembled into tube sections required for the construction of the heat exchanger body, and the tube sections are then mounted on the heat exchanger body and on the heat exchanger. The heat exchanger is the main component of the oxygenator. In this connection, reference is made to WO 2011/086 010 A1.

The invention claimed is:

1. A heat exchanger tube for a heat exchanger of an oxygenator, comprising
   a tube body made of a thermoplastic polyurethane (TPU) that is free of gel particles,
   wherein the tube body (2) has a Shore hardness greater than 60 D, and
   wherein a wall thickness of the tube body deviates less than 0.02 mm along a length of the tube, and
   wherein the wall thickness of the tube body is less than 0.07 mm, and
   wherein the heat exchanger tube has a dielectric strength of at least 10 kV.

2. The heat exchanger tube according to claim 1, wherein the Shore hardness of the tube body (2) is greater than 70 D.

3. The heat exchanger tube according to claim 2, wherein the Shore hardness of the tube body (2) is between 75 D and 83 D.

4. The heat exchanger tube according to claim 1, wherein the tube body comprises amorphous material regions.

5. The heat exchanger tube according to claim 1, wherein the wall thickness of the tube body deviates less than 0.01 mm along the length of the tube.

6. The heat exchanger tube according to claim 1, wherein the wall thickness is between 0.05 mm and 0.06 mm.

* * * * *